United States Patent [19]

Fawzi et al.

US005373022A

[11] Patent Number: 5,373,022
[45] Date of Patent: Dec. 13, 1994

[54] SALTS/ION PAIRS OF NON-STEROIDAL ANTI-INFLAMMATORY DRUGS IN VARIOUS DOSAGE FORMS

[75] Inventors: Mahdi B. Fawzi, Flanders; Majid Mahjour, Netcong, both of N.J.

[73] Assignee: The Warner-Lambert Company, Morris Plains, N.J.

[21] Appl. No.: 942,108

[22] Filed: Sep. 8, 1992

Related U.S. Application Data

[63] Continuation of Ser. No. 664,018, Mar. 4, 1991, abandoned.

[51] Int. Cl.$^5$ ............................................. A61K 31/19
[52] U.S. Cl. ..................................................... 514/570
[58] Field of Search ............................................ 514/570

[56] References Cited

U.S. PATENT DOCUMENTS 4,783,465  11/1988  Sunshine et al. .................... 514/255

*Primary Examiner*—S. J. Friedman
*Attorney, Agent, or Firm*—Craig M. Bell

[57] ABSTRACT

Novel pharmaceutical compositions are comprised of the salt or ion pair formation of a non-steroidal anti-inflammatory drug and an antihistamine or other decongestant. The physico-chemical characteristics of these compositions show them to be substantially different from their parent acid or base and will enable the preparation of dual action sustained or enhanced relief therapy regimens. The compositions also possessed enhanced stability and therefore the multi-symptom relief can be incorporated into a number of dosage forms such as capsules, tablets, elixirs, ointments and the like.

3 Claims, 20 Drawing Sheets

SALTS/ION PAIRS OF NON-STEROIDAL ANTI-INFLAMMATORY DRUGS IN VARIOUS DOSAGE FORMS

This application is a continuation of U.S. patent application Ser. No. 07/664,018, filed on Mar. 4, 1991, now abandoned.

BACKGROUND OF THE INVENTION

Salt formation is an acid-base reaction involving either a proton-transfer or neutralization reaction and is therefore controlled by factors influencing such reactions. Theoretically, every compound that exhibits acid or base characteristics can participate in salt formation. Particularly important is the relative strength of the acid or base and the acidity and basicity constants of the chemical species involved. These factors determine whether or not salt formation occurs and are a measure of the stability of the resulting salt. The salt form is known to influence a number of physico-chemical properties of the parent compound including dissolution rate, solubility, stability, and hygroscopicity. Salt formation is useful in pharmaceutical formulations since these properties, in turn, affect the availability and formulation characteristics of the drug.

Higuchi et al. Anal. Chem. 39; 974–979 (1967) discloses the physicochemical basis behind the ion-pair extraction of pharmaceutical amines and suggests the use of ion-pairing for the improvement of drug lipophilicity and absorption. European patent 96,013 to Casini et al. discloses the preparation of novel salts of Erythromycin A with acetylsalicylic acid that has antipyretic and anti-inflammatory activity and with DL-alpha mercaptopropionyl glycine with mucolytic and hepatoprotective activity. These compounds allegedly have the pharmacological activity of the antibiotic moiety as well as that of the acidic moiety. These new salts also allegedly have physico-chemical properties different from both erythromycin A and the acidic moeity.

French patent no. 1,479,209 discloses codeine acytylsalicylate as a new salt having analgesic, anti-inflammatory and cough suppressant activities that also modifies bronchial secretions. U.S. Pat. No. 4,816,247 to Desai et al and U.S. Pat. No. 4,515,811 to Halton et al. disclose pharmaceutical applications of salt formation. U.S. Pat. No. 4,563,443 to Gobetti et al. and U.S. Pat. No. 4,521,538 to Baglioni et al. disclose new derivatives of known drugs by the formation of ester and thioester linkages of known compounds. Japanese patent no. 13273/65 discloses a salt of glycyrrhetic acid with beta-dimethyl aminoethyl benzhydryl ether with allegedly greater anti-inflammatory and antihistamine activities than its individual pharmaceutical components. The compounds dissolve slowly in acid and alkali thus giving sustained release action of the active component upon oral administration.

For purposes of this disclosure, the term salt/ion pair is used to refer to the fact that the new chemical entities produced by the acid-base reaction exists in either the solid crystalline form "salt" or as an amorphous, semi-solid viscous mass "ion-pair".

It is an object of the present invention to prepare novel salts of non-steroidal anti-inflammatory agents together with an antihistamine, sympathomimetic drug, cough suppressant or expectorant together with a pharmaceutically acceptable, non-toxic carrier. These novel pharmaceutical compositions allow for the use of a single new compound in place of the physical mixtures of several compounds found in the prior art. The novel pharmaceutical compositions also possess solubilities different from those of the individual drug components which enables the easier preparation of sustained or enhanced release dosage forms. And surprisingly, the compounds of the present invention do not exhibit the pharmaceutical incompatabilities expected when the sodium salt of an anti-inflammatory drug is combined with the strong acid salts of an antihistamine.

It is a further object of the present invention to prepare novel salts/ion pairs of non-steroidal anti-inflammatory drugs with non-sedating antihistamines and decongestants with unique physico-chemical properties over the multi-symptom relief medicines known in the art. Specifically, non-steroidal anti-inflammatory drugs such as meclofenamic acid, salicylic acid, ibuprofen, naproxen, dichlofinac, sulindac and aspirin are used to form novel salt/ion pairs with antihistamines and decongestants such as Diphenhydramine, Pseudoephedrine, Hismanal, Terfenadine, Loratidine, Ranitidine, Cimetidine, etc.

Meclofenamic acid is an antiflammatory and antipyretic compound with the following formula:

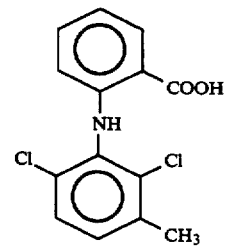

Naproxen is a non-steroidal, anti-inflammatory analgesic and antipyretic with the following formula:

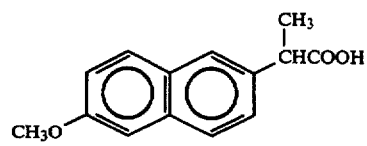

Sulindac is also an anti-inflammatory drug with the following structure:

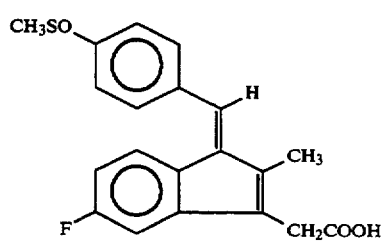

Salicyclic acid is a topical keratolytic with the following structure:

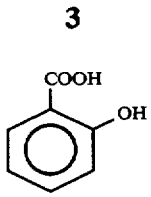

Ibuprofen is a non-steroidal anti-inflammatory compound with the following structure:

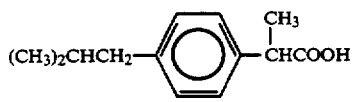

Diphenhydramine, Pseudoephedrine, Hismanal and Terfenidine are all antihistamines with the following respective formulas:

Diphenhydramine

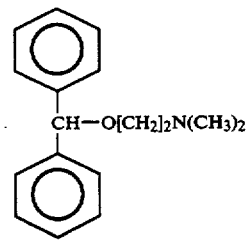

Pseudoephedrine

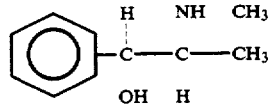

Hismanal

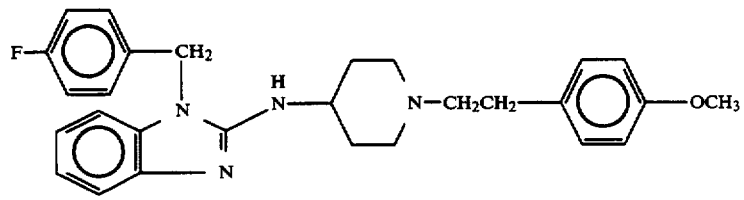

Terfenidine

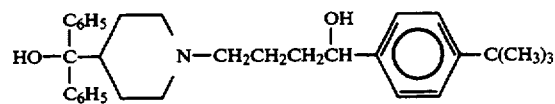

SUMMARY OF THE INVENTION

Several pharmaceutical formulations comprising new salts/ion-pairs of non-steroidal anti-inflammatory drugs have been prepared with antihistamines or decongestants. The melting points, solubilities, spectra (NMR, UV, IR), thermal characteristics, and crystalline structure of these new chemical entities confirm that they are physicochemically different than the parent acid or base. The characterization and identification test results for two solid and one semi-solid salt/ion-pair, Meclofenamic acid/Diphenhydramine, Salicylic acid/Diphenhydramine and Sulindac/Pseudoephedrine, respectively, are provided. Incorporation of these novel compounds into various dosage forms provide an advantage over existing multi-symptom preparations, such as cold/flu remedies, as a result of their unique physicochemical properties.

DETAILED DESCRIPTION OF THE INVENTION

The objective of the present invention is to cover the use of novel salts (or ion-pairs) of non-steroidal anti-inflammatory agents prepared with an antihistamine such as Diphenhydramine, (including also Ranitidine, Loratidine and Cimetidine), a sympathomimetic drug (nasal decongestant, bronchodilator), a cough suppressant or expectorant, in combination with suitable, pharmaceutically acceptable non-toxic carriers or excipients. The novel salts can be incorporated into various dosage forms including capsules, tablets, elixirs, parenterals, transdermal patches, suspensions, saches, suppositories, topicals, etc. for use in the treatment of cough, cold, cold-like and/or flu symptoms. Either of the individual compounds used to prepare the novel salt/ion-pair of the non-steroidal anti-inflammatory drug could be present in the composition as the free form or as an acceptable salt thereof. The novel salts/ion-pairs can also be combined with other drugs in a dosage form.

The non-steroidal anti-inflammatory drug of interest is dissolved in an organic solvent together with an equivalent amount of the antihistamine sympathomimetic drug or cough suppressant. The solution is then evaporated under a nitrogen atmosphere at room temperature to a liquid/semi-solid viscous mass. The compound is then crystallized through the use of a suitable organic solvent such as alcohol, alcohol/water etc. The remainder of the liquid can be driven off through the continued application of heat. The compound is then formulated into any one of a number of known dosage forms or delivery systems by means known in the art. The following examples are provided to illustrate specific embodiments of the compositions of the present invention. They are to serve as illustrations only, and it is realized that minor changes and modifications are possible and should not be regarded as falling outside the spirit and scope of the present invention as later defined by the following claims.

EXAMPLE I

Diphenhydramine base and Pseudoephedrine base were extracted and collected by filtration of the alkalinized solutions of their respective salts. Sulindac (SST Corp., Clifton, N.J.) was then dissolved in methyl acetate/methoxyethanol (60/40) and an equimolar amount of Pseudoephedrine was added with stirring. A clear solution was obtained and the solvent then evaporated to yield a dark-orange semi-solid form.

a) In order to analyze to what extent a new chemical entity was formed, Fourier Transform Infrared Spectroscopy (FTIR) was utilized in order to compare the characteristics of the salt/ion pair with that of the individual components. Potassium bromide (KBr) pellets were made of each. For the semi-solid drug/antihistamine material, a solution of the material in methylene chloride was titrated into KBr followed by solvent evaporation and conventional pellet formation.

Figure 1A:
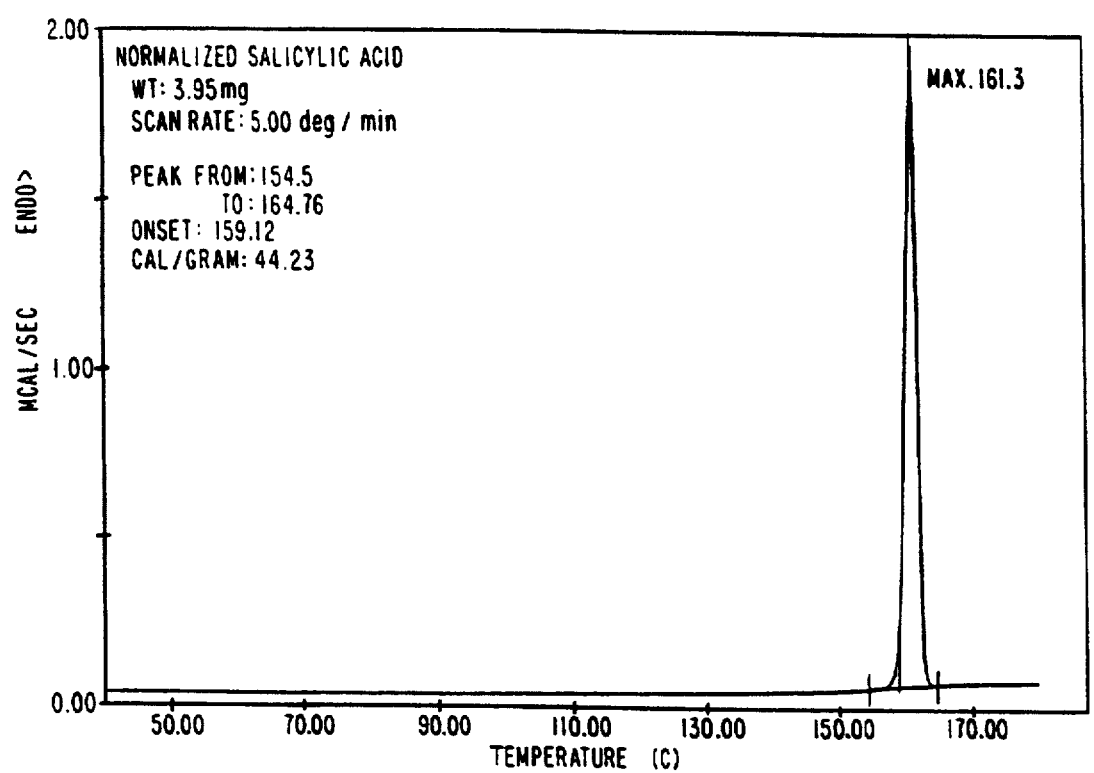
FIGS. 1a and 1b represent Differential Scanning Colorimetry (DSC) Thermograms of Salicyclic Acid alone and the Salicyclic Acid/Diphenhydramine salt of the present invention, respectively.
Figure 1B:
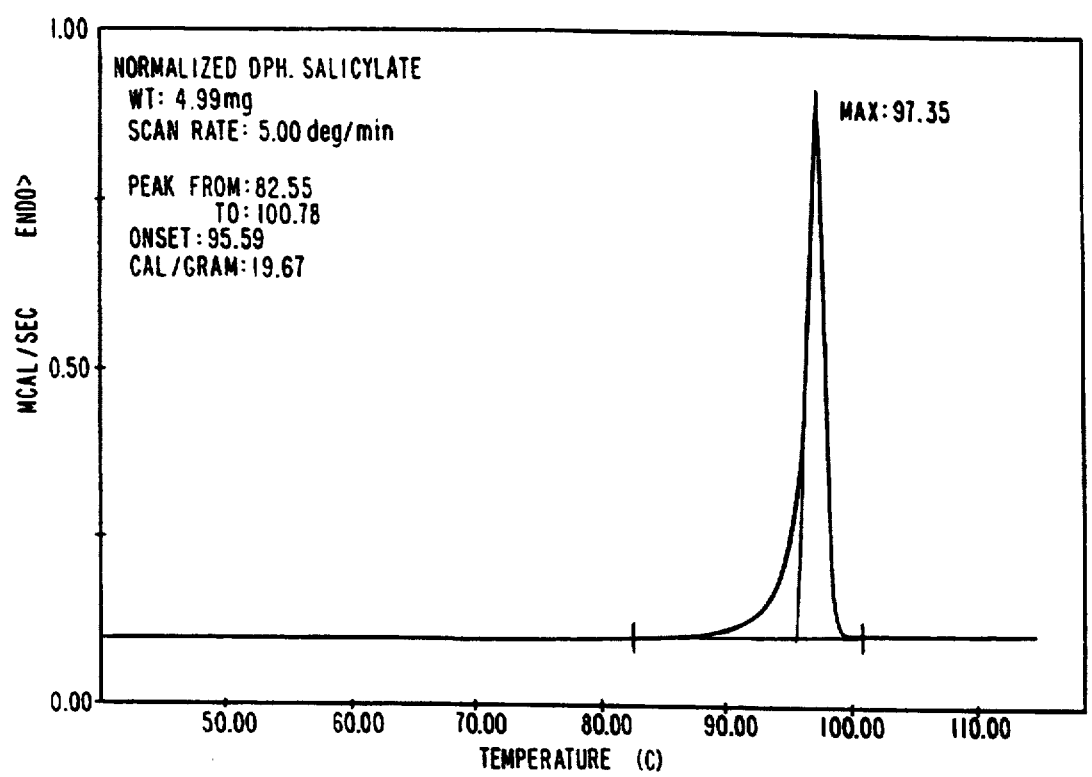

The resulting spectra are shown in FIG. 1 and the peaks of interest are presented in Table 1 for the salt/ion-pair and the physical mixture of Pseudoephedrine (PSEU) and Sulindac (SUL). The physical mixture yielded a spectrum which is simply the sum of the spectra of the individual components, whereas the salt/ion-pair (SUL/PSEU) spectrum shows a shift in the carbonyl group from 1700 to 1587 nm. This shift in the spectrum confirms that a chemical reaction between SUL and PSEU occurred to yield the resulting salt/ion-pair.

TABLE 1

| IR Spectra of Sulindac, Pseudoephedrine as Salt/Ion Pair or Physical Mixture | | | | |
|---|---|---|---|---|
| PEAK | SUL | PSEU | MIXTURE | SUL/PSEU |
| C = O | 1701 | NA | 1700 | 1587 |

Figure 2:
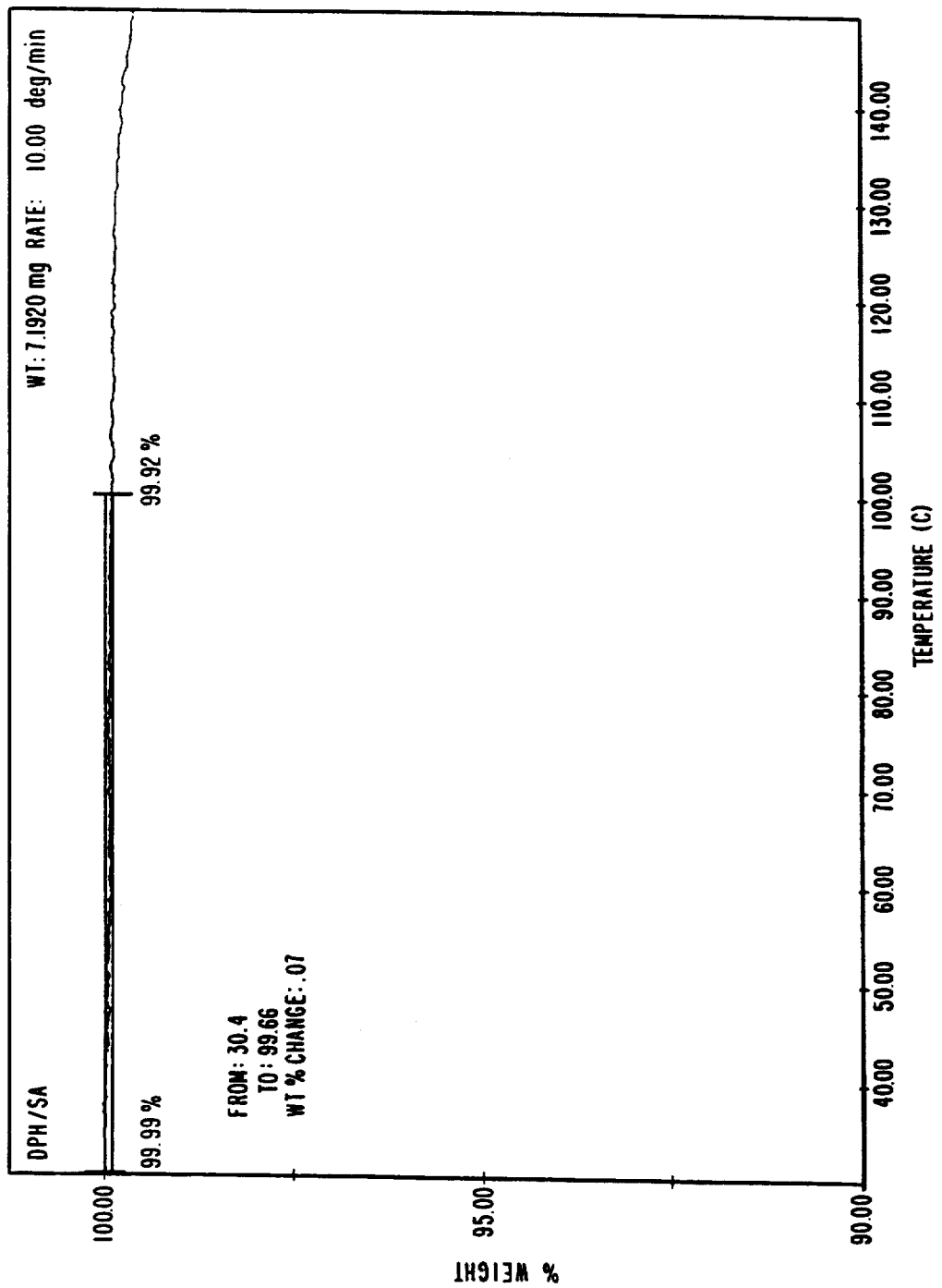
FIG. 2 represents a Thermogravimetric Analysis (TGA) Thermogram of the Salicyclic Acid/Diphenhydramine salt of the present invention.
Figure 3A:
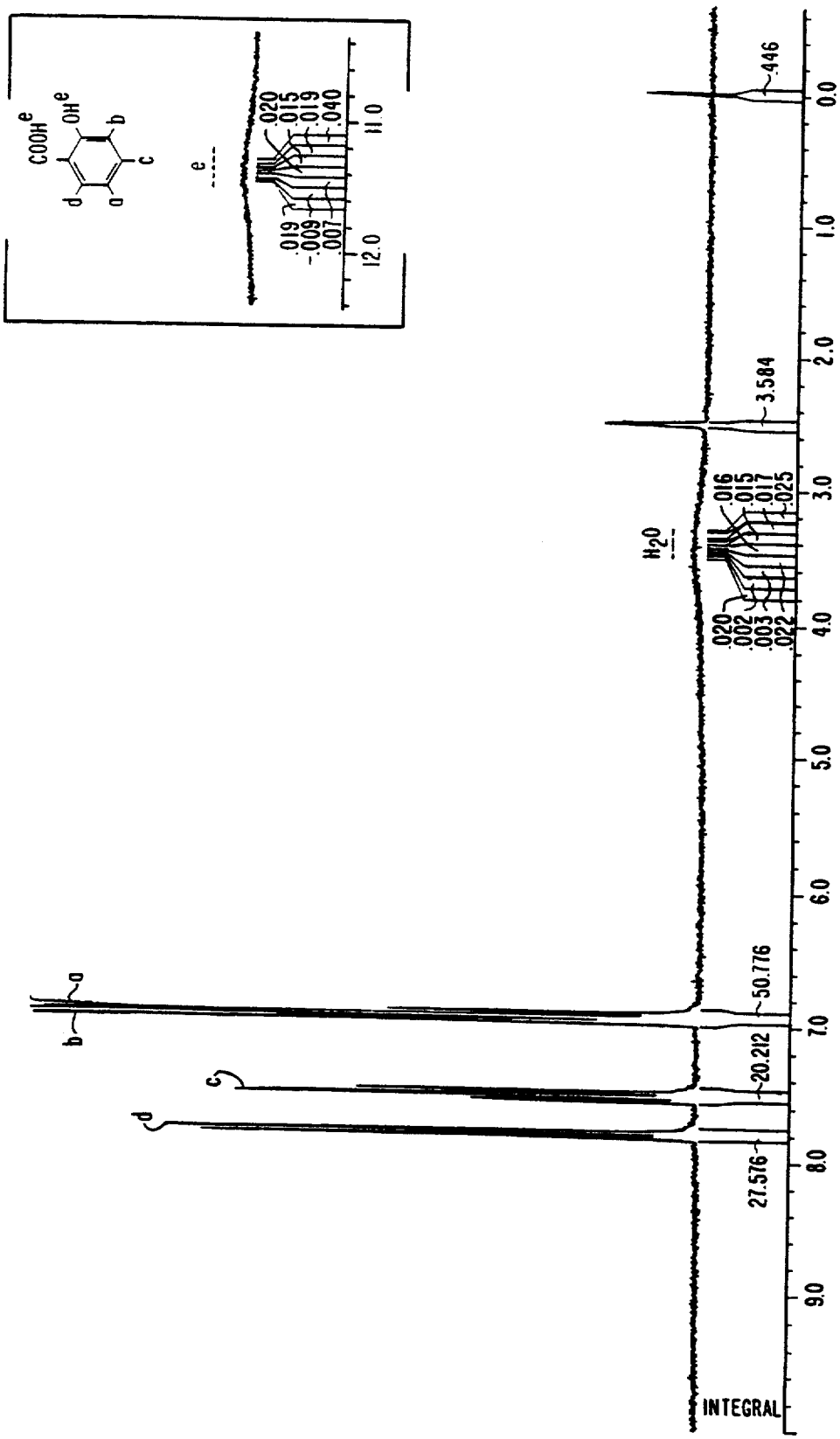
FIGS. 3a, 3b and 3c represent three (3) comparative Proton NMR spectra of Salicylic Acid, Diphenhydramine and the Salicylic Acid/Diphenhydramine salt of the present invention.
Figure 3B:
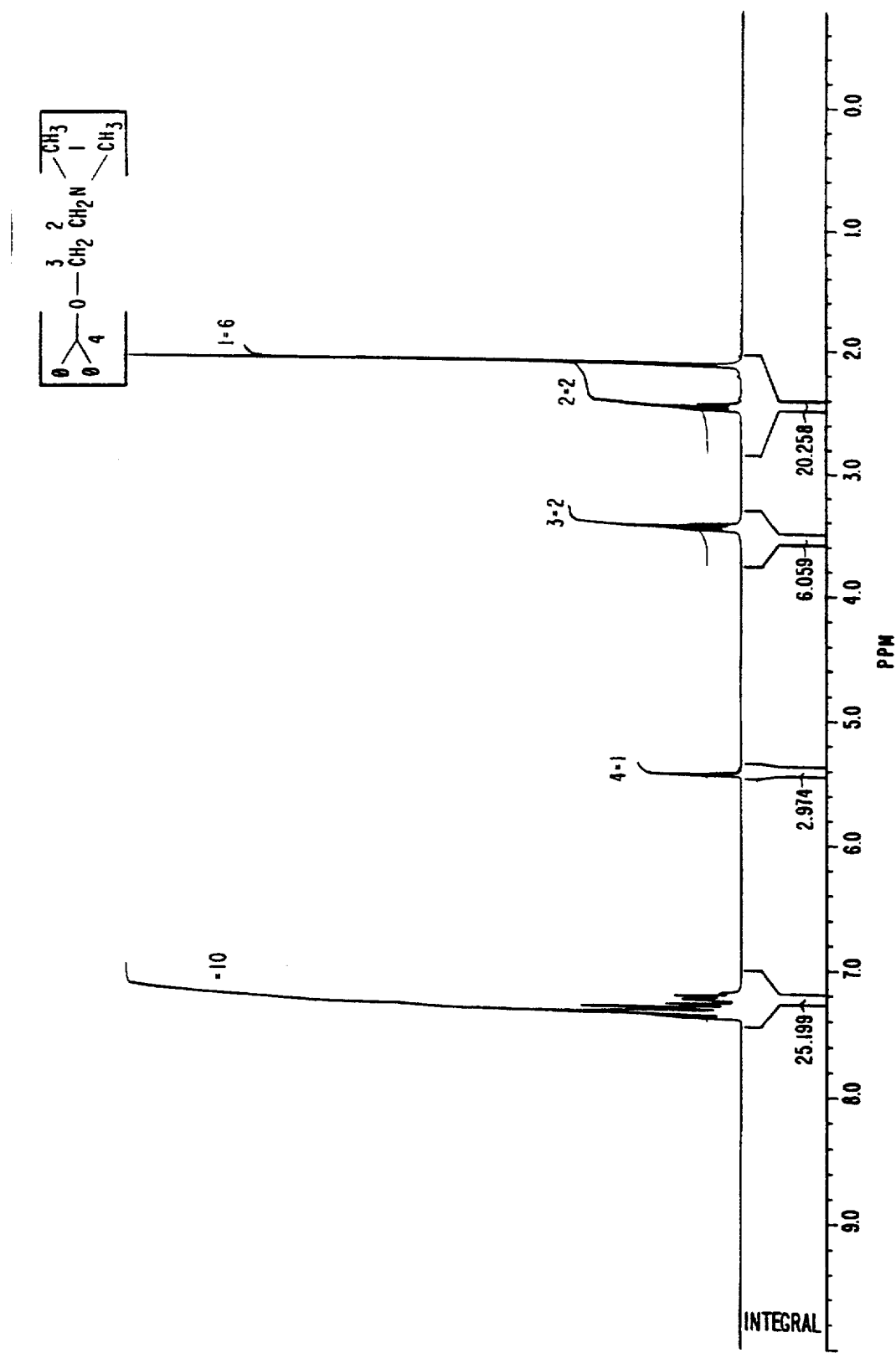
Figure 3C:
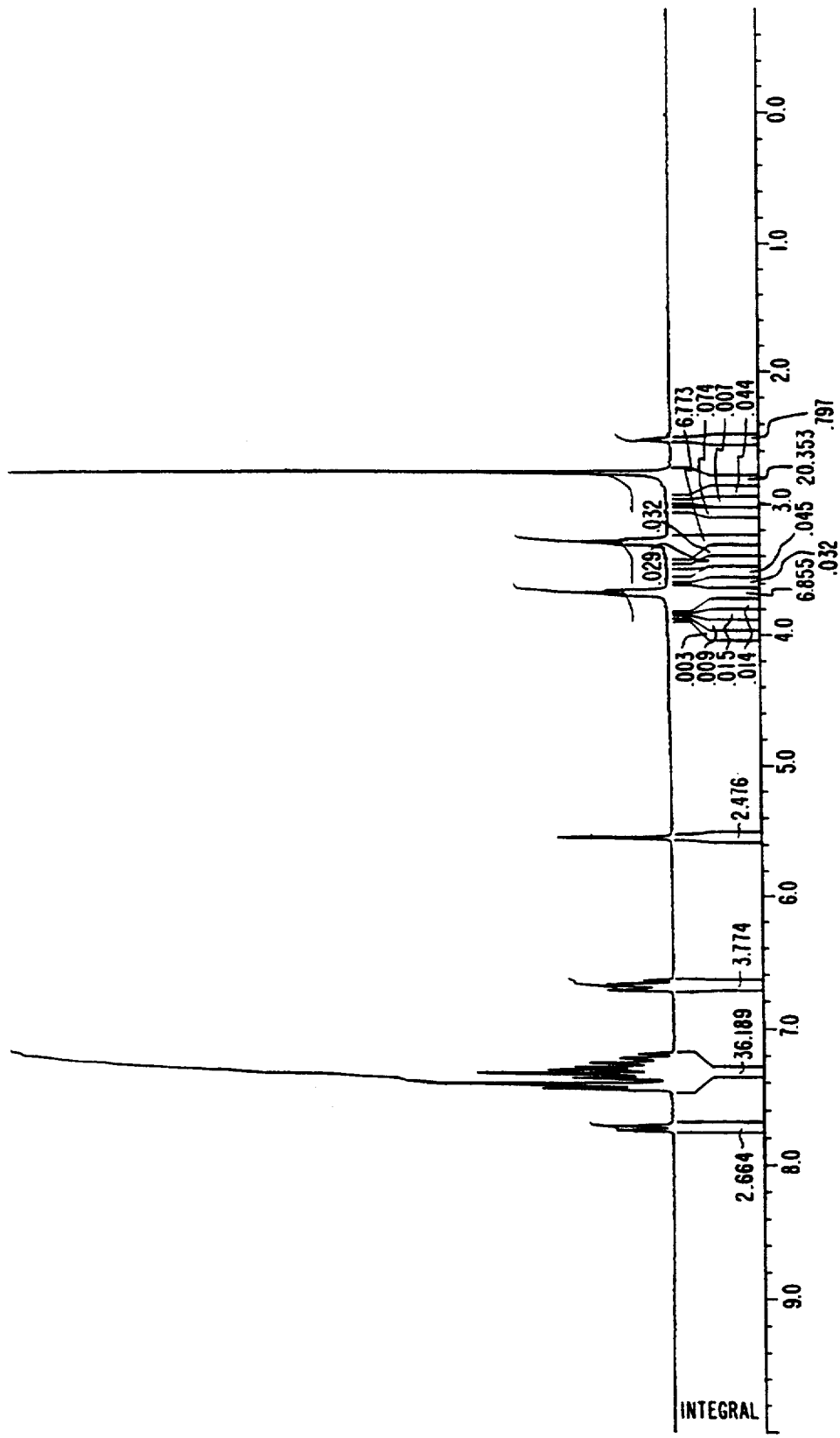

EXAMPLE II a) The Salicylic acid - Diphenhydramine salts (SA/DPH) were prepared in a similar manner to the compounds in Example I. The dried material collected after solvent evaporation was a crystalline, off-white particle with a particle size ranging from 10–50 microns. The melting range as measured using a Metter Hot Stage FP2 for the Salicylic acid-diphenhydramine salt is 99°–107° C., which is lower than the melting range of Salicylic acid (158°–61° C.) and higher than Diphenhydramine base (liquid at room temperature). The distinctly different melting point for SA/DPH indicates that it is a new chemical entity.

b) Differential Scanning Calorimetry (DSC) was performed at a rate of 5°/min under nitrogen atmosphere using a Perkin Elmer DSC 2 ®. DSC revealed one endothermic peak with an onset of 95.6° C. for SA/DPH. Salicylic acid alone had one sharp endothermic peak with onset at 150.1° C. (FIG. 2). DSC confirms that SA/SPH exists as one new compound.

c) Thermogravimetric analysis (TGA) was conducted and the Salicylic acid - Diphenhydramine salt TGA showed a weight loss of 0.07% over the temperature range of 30°–100° C. indicating a trace amount of water or solvent in the SA/DPH (FIG. 3). Results of experimental elemental analysis were in close agreement with theoretical values for the salt/ion pair of SA/SPH.

TABLE 2

Figure 4A:
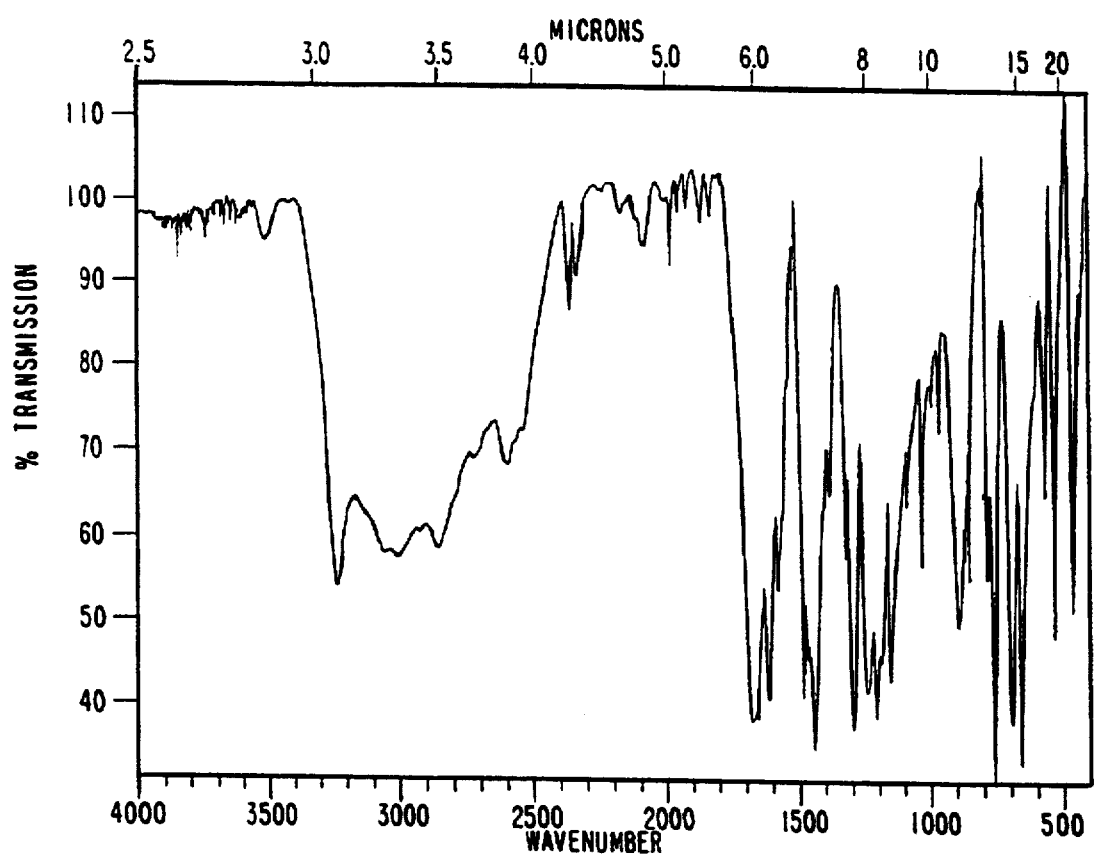
FIGS. 4a and 4b present FTIR spectra for Salicyclic Acid and the Salicylic Acid/Diphenhydramine salt of the present invention, respectively.
Figure 4B:
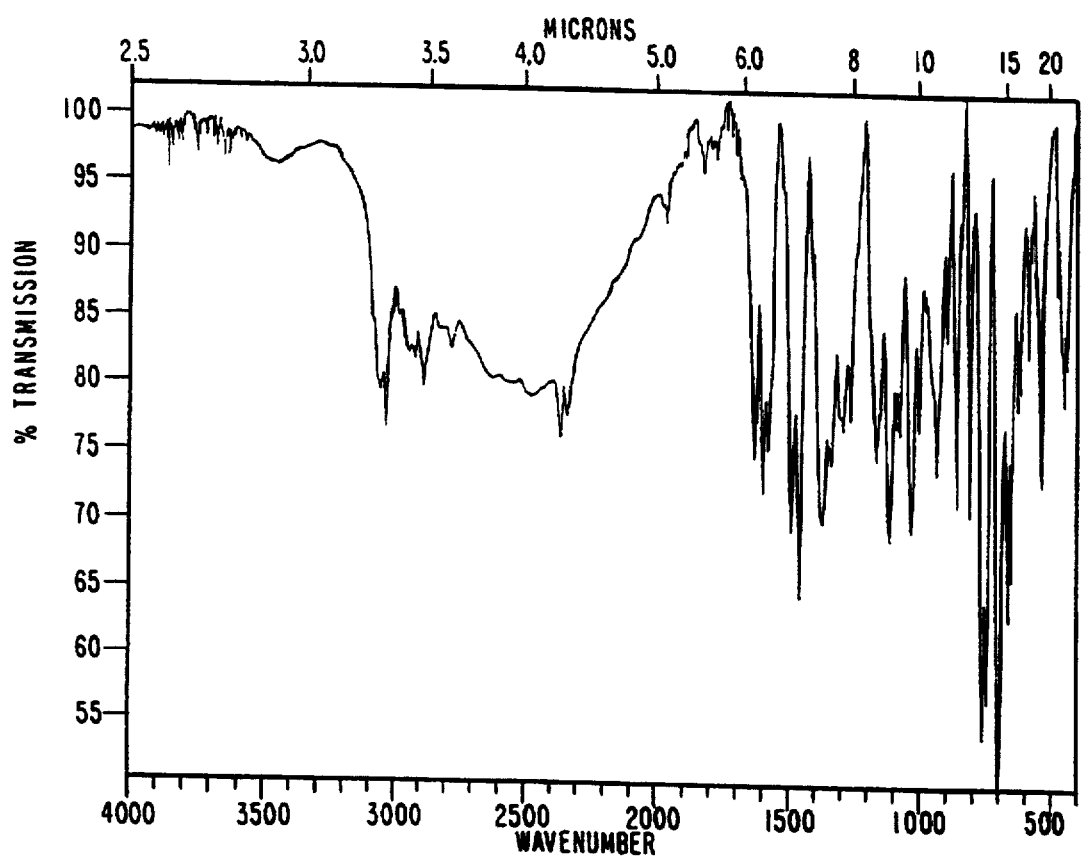
Figure 5A:
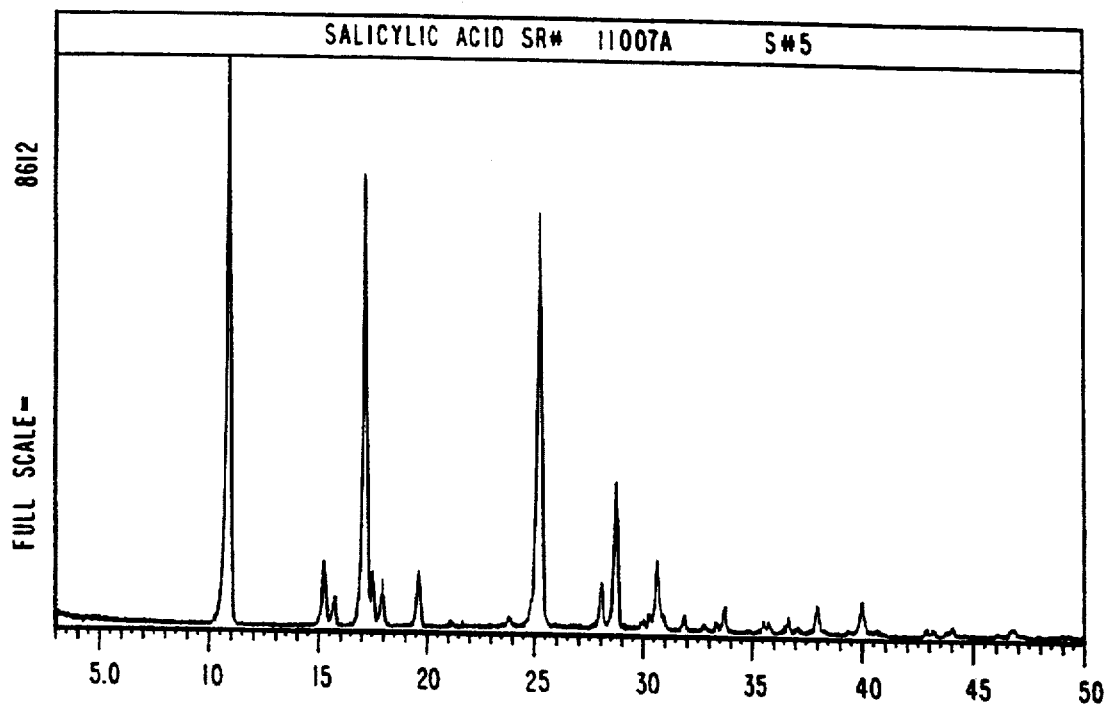
FIGS. 5a and 5b represent comparative X-ray Diffractogram patterns for Salicylic Acid and the Salicylic Acid/Diphenhydramine salt of the present invention, respectively.
Figure 5B:
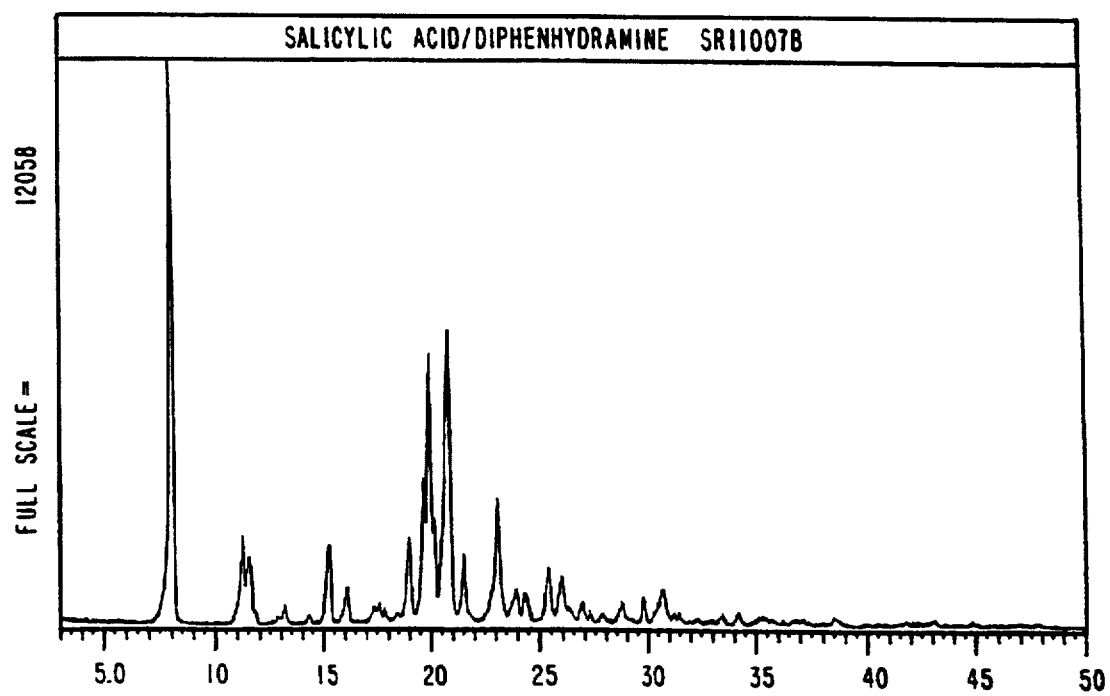

| Elemental Analysis of SA/DPH | | | |
|---|---|---|---|
| | % C | % H | % N |
| Theoretical | 73.19 | 6.86 | 3.56 |
| Experimental | 73.34 | 6.90 | 3.43 | d) Nuclear Magnetic Resource (NMR) was performed on a proton spectrometer. The NMR spectra for Salicylic acid, Diphenhydramine and the Salicylic acid-Diphenhydramine salts are shown in FIG. 4. A slight upfield shift for the aromatic protons of SA and a significant downfield shift for the aliphatic protons of DPH were observed for the SA/DPH sample. The shifts on the NMR spectra observed for SA/DPH are indicative that a chemical reaction has occurred, such as a proton transfer.

e) The compounds were then subjected to Fourier Transform Infrared Spectroscopy (FTIR) using a Cygnus 100 FTIR. Potassium bromide (KBr) pellets were made with the drugs as before and the infrared spectra for SA and SA/DPH are shown in FIG. 5. The characteristic carbonyl stretching peak of Salicylic acid shifted from 1675 nm to 1627 nm for SA/SPH. This shift in the FTIR spectra indicates that a chemical reaction occurred in the formation of the new salt/ion-pair of SA/DPH.

f) Ultraviolet (UV) absorbence spectra were also obtained for the Salicylic acid-Diphenhydramine salts and compared with that of the individual components in methanol at equimolar concentrations. The absorbence maxima and absorptivity for the compounmds is summarized in Table 2.

TABLE 2

| UV Absorptivity of SA/DPH | | |
|---|---|---|
| Compound | Abs. Max(nm) | Absorptivity(l/g-cm) |
| SA | 304 | 26.77 |
| SA/DPH | 298 | 8.19 |

The UV spectra clearly shows a shift in the absorbtion maximum ($\lambda$ max) of from 306 to 298. The shift in both the absorbance maximum and the absorbtivity spectra also prove the formation of a new chemical entity.

g) Equimolar solutions of the individual components and the Salicylic acid-Diphenhydramine salt/ion pairs were also compared through thin layer chromatography (TLC) analysis using a silica gel 60F254 plate from EM Science (0.25 mm) and resolved in a saturated chamber of methanol, isopropanol or a mixture of ethyl acetate:methanol:ammonium hydroxide in a 8:2:1 molar ratio. Component zones were then visualized using ultraviolet light and iodine vapor. TLC analysis of the SA/DPH compound revealed two solutes whose Rf values matched that of the free acid and base.

The solubilities of the Salicylic acid-Diphenhydramine salts/ion pairs in water at room temperature were estimated by placing an excess of the compound in a scintillation vial containing a few milliliters of water followed by overnight shaking. The samples were filtered through an 0.45 um nylon filter and the filtrates analyzed for the Diphenhydramine concentration by HPLC.

The solubility of SA/DPH in water at room temperature as calculated from the DPH concentration is shown in Table 3. SA/DPH is soluble in polar organic solvents. The marked increase in the aqueous solubility of DPH due to the formation of the SA/DPH salt/ion-pair is clearly indicative of the existence of a chemical entity completely different from the parent base or acid.

TABLE 3

Figure 6A:
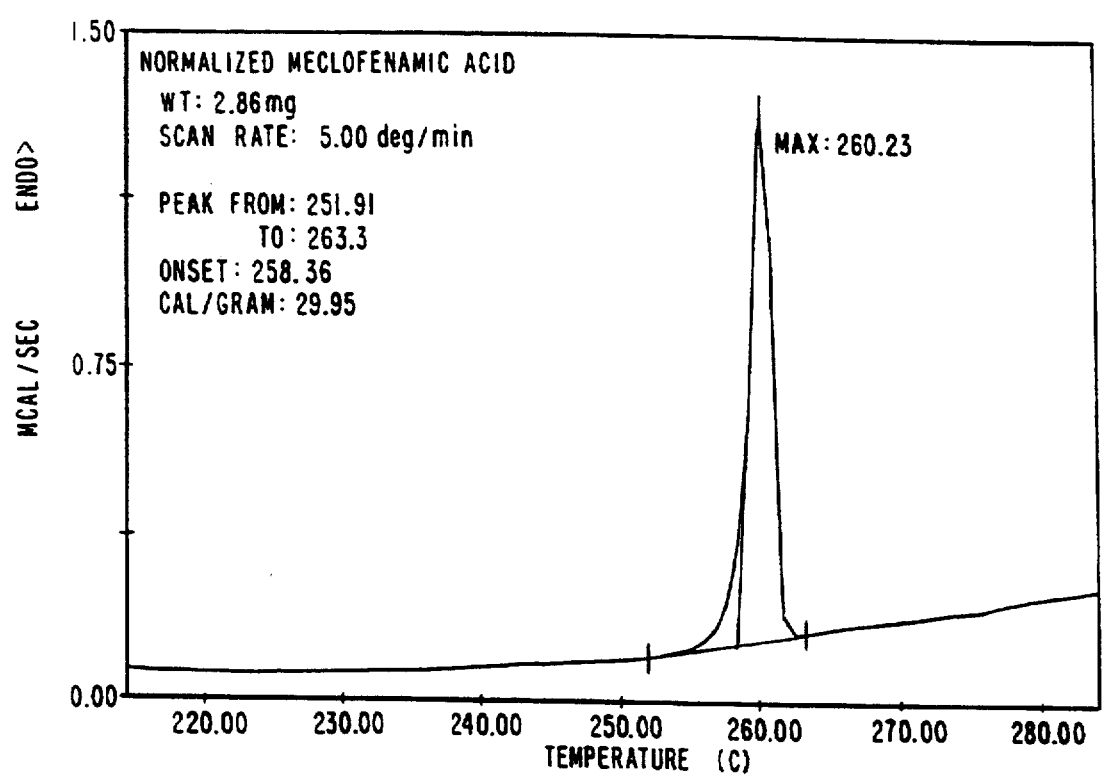
FIGS. 6a and 6b represent comparative DSC thermograms for Meclofenamic Acid and the Meclofenamic Acid/Diphenhydramine salt/ion pair of the present invention, respectively.
Figure 6B:
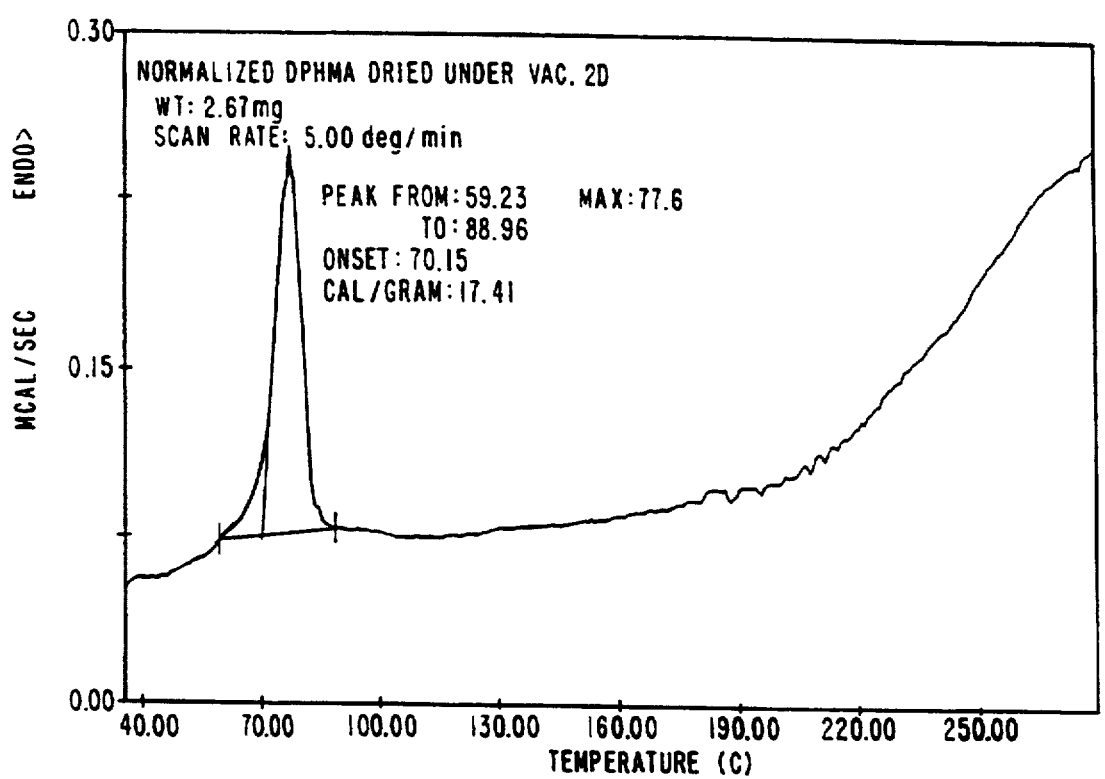

| Solubility of SA/DPH in Water | |
|---|---|
| COMPOUND | R.T. SOLUBILITY ($\mu$g/ml) |
| DPH | 275 |
| SA/DPH | 2827 |
| SA | 2174 (4) | h) X-ray diffractograms were obtained for the Salicylic acid-Diphenhydramine salts and compared with that of Salicylic acid alone. Pressed powder samples were scanned at a rate of 5 deg/min from 3 deg to 50 deg (2-theta) with the detector sampling interval set at 0.02 deg. A copper source operating at a 40 kV/40 mA power level was used to generate the x-rays. The x-ray diffractograms obtained for Salicylic acid and DPH/Salicylic acid are shown in FIG. 6. The diffractograms show no overlap in major peaks between the compounds. Four minor peaks of Salicylic acid were found to match in the diffractogram of SA/DPH indicating that a portion of the original Salicylic acid crystalline structure remains intact in the SA/DPH compound. The diffractograms confirm that the crystalline structure of SA/DPH is completely different than that of SA.

EXAMPLE III

Figure 7:
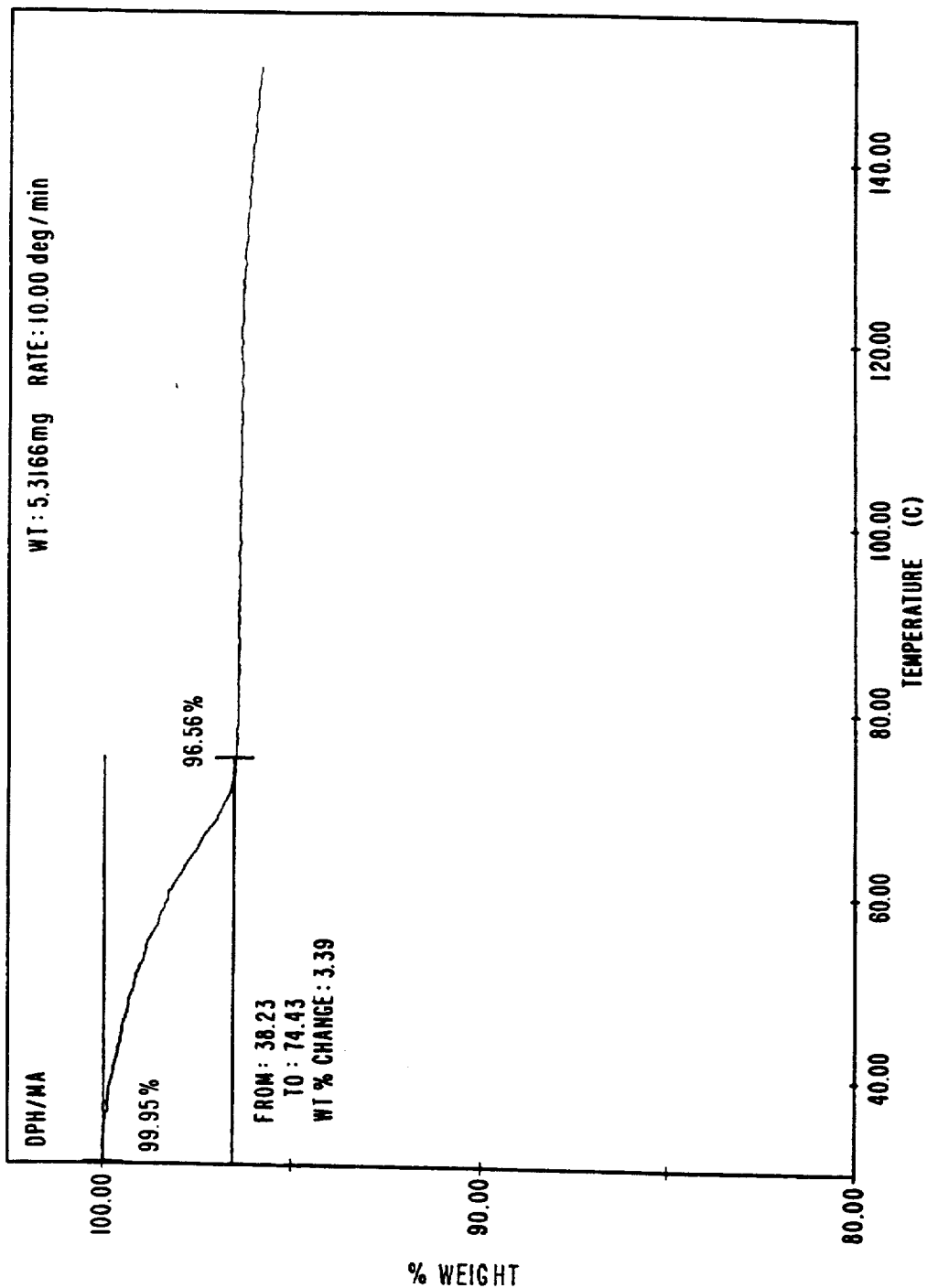
FIG. 7 represents a TGA Thermogram for the Meclofenamic Acid/Diphenhydramine salt/ion pair of the present invention.
Figure 8A:
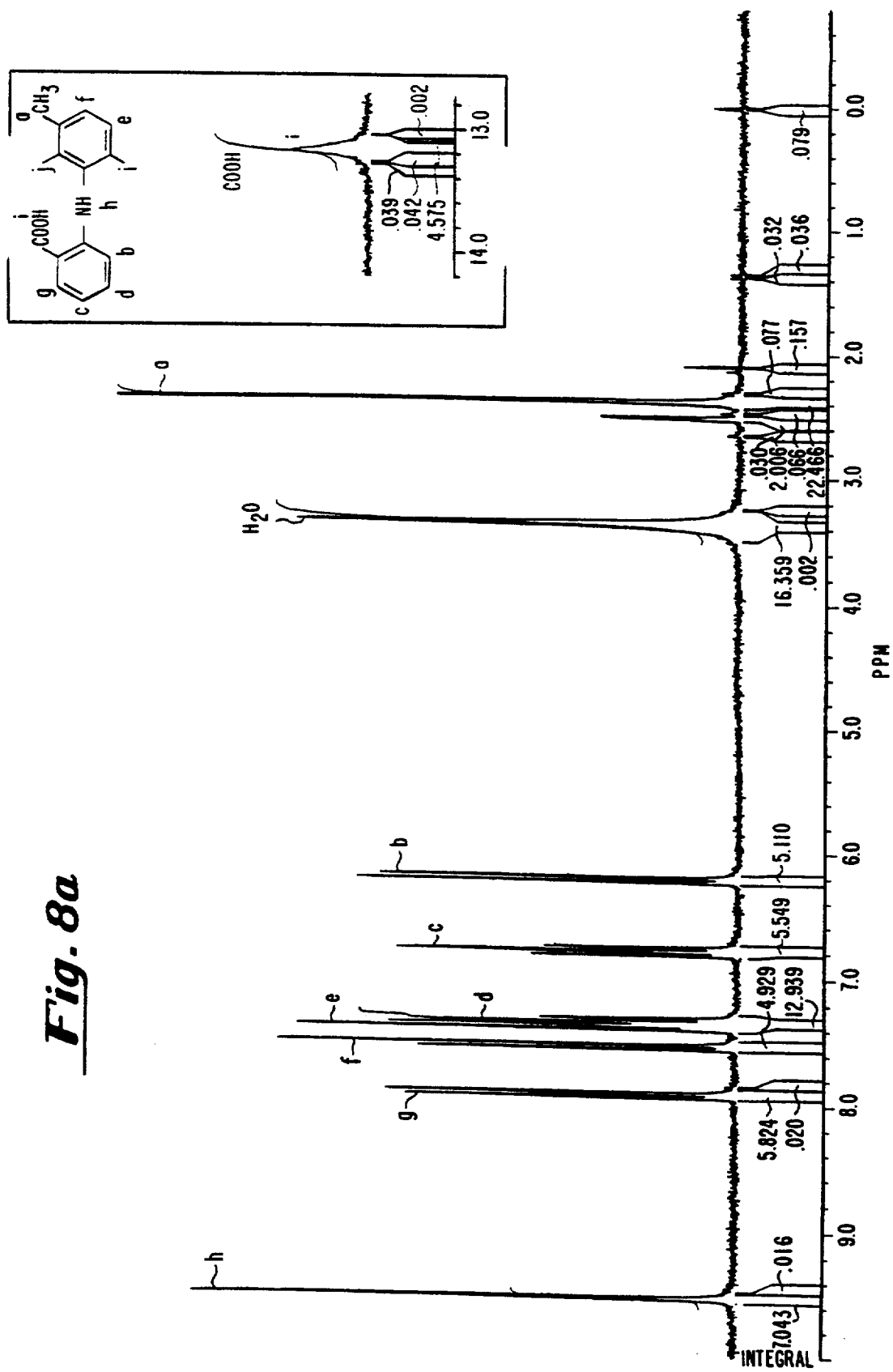
FIGS. 8a, 8b and 8c represent comparative Proton NMR spectra for Meclofenamic Acid, Diphenhydramine and the Meclofenamic Acid/Diphenhydramine salt/ion pair of the present invention, respectively.
Figure 8B:
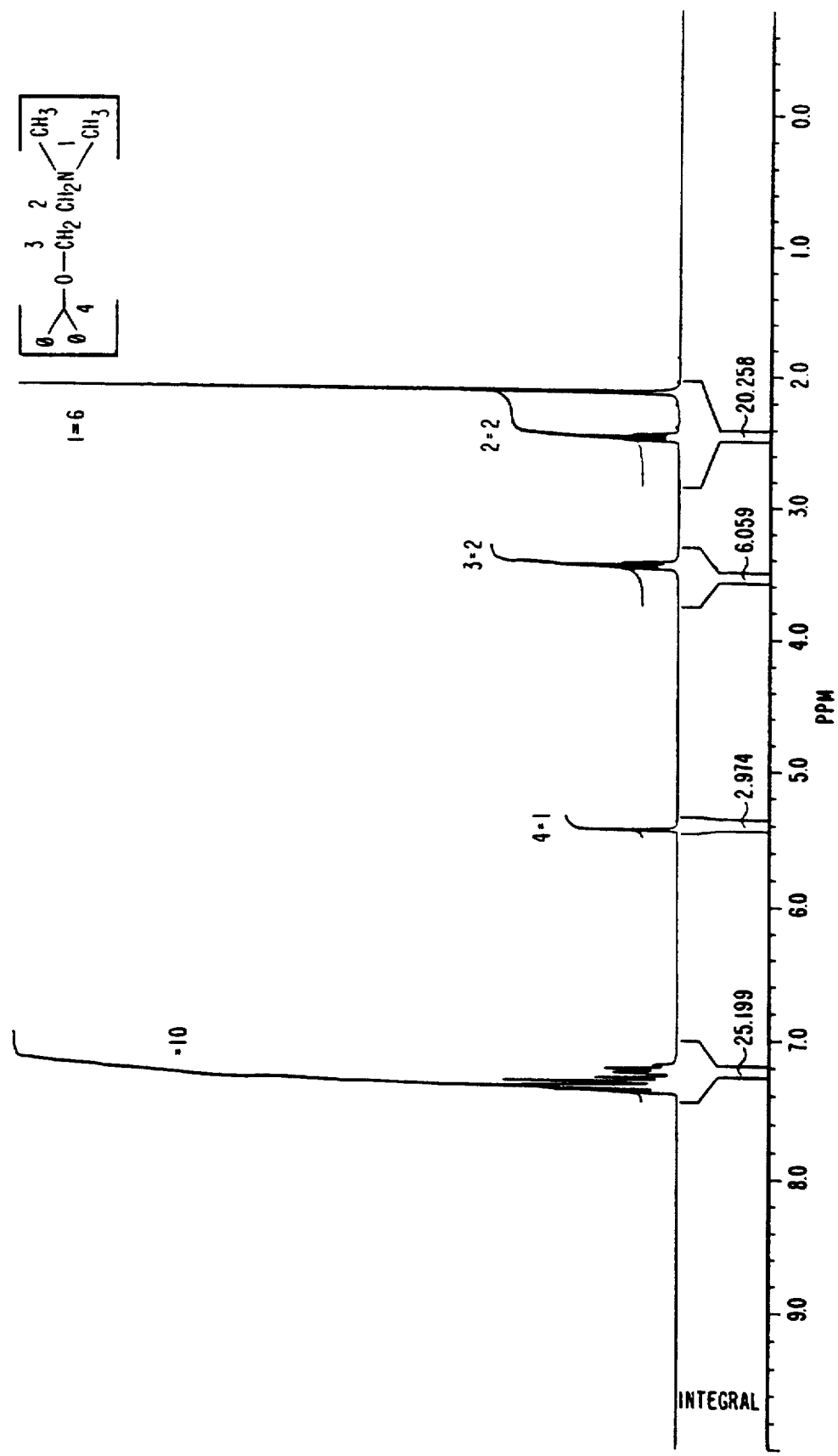
Figure 8C:
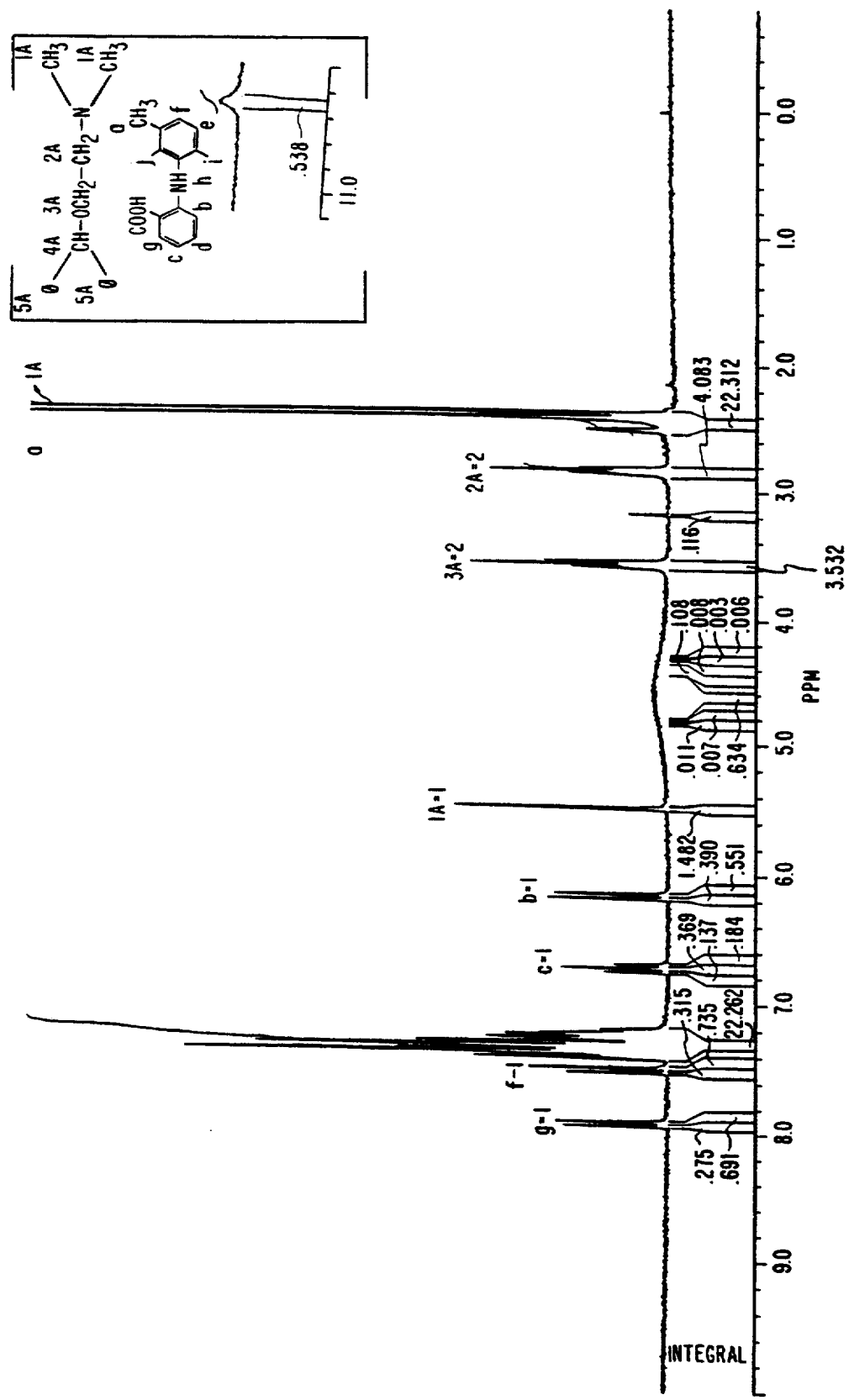

Meclofenamic acid and Diphenhydramine Hydrochloride were obtained from the Warner-Lambert Co., Holland, Mich. The salt/ion pair compositions were made according to the procedure set forth in Example I and a white crystalline powder was obtained with a particle size ranging from 10 to 40 microns.

a) The melting point ranges for the compound and its individual components was determined using a Metler Hot Stage FP2. The melting point range for Meclofenamic acid-Diphenhydramine (MA/DPH) is 76°–80° C. which is lower than than of MA (257°–259° C.) and higher than DPH base (liquid at room temperature). The distinctly different melting point for MA/DPH indicates that it is a different chemical entity than either parent compound.

b) Differential Scanning Colorimetry (DSC) showed one endothermic peak from 47.46°–86.42° C. with an onset of 66.24° C. Meclofenamic acid alone had one sharp endothermic peak from 251°–263° C. with an onset at 258.4° C. (FIG. 7). DSC confirms that MA/DPH exists as one new chemical entity.

c) Thermogravimetric analysis (TGA) was performed at a rate of 10 deg./min under a nitrogen atmosphere as in Examples I and II. The results showed a weight loss of 3.39% in the temperature range 30°–74° C. indicating a small amount of water or solvent present (FIG. 8).

d) Results of experimental elemental analysis, shown in Table 4, are in close agreement of the predicted values when adjusted for 1 mole of water.

TABLE 4

Figure 9A:
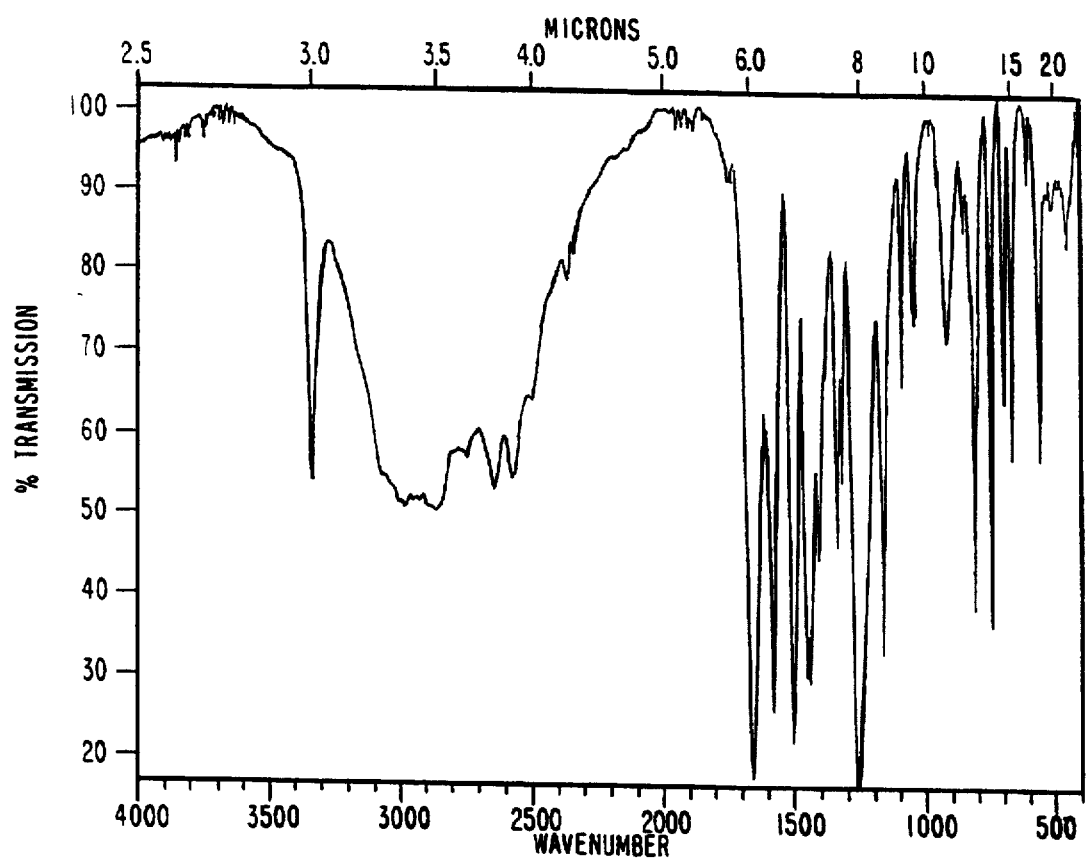
FIGS. 9a and 9b represent the FTIR spectra of Meclofenamic Acid and the Meclofenamic Acid/Diphenhydramine salt/ion pair of the present invention, respectively.
Figure 9B:
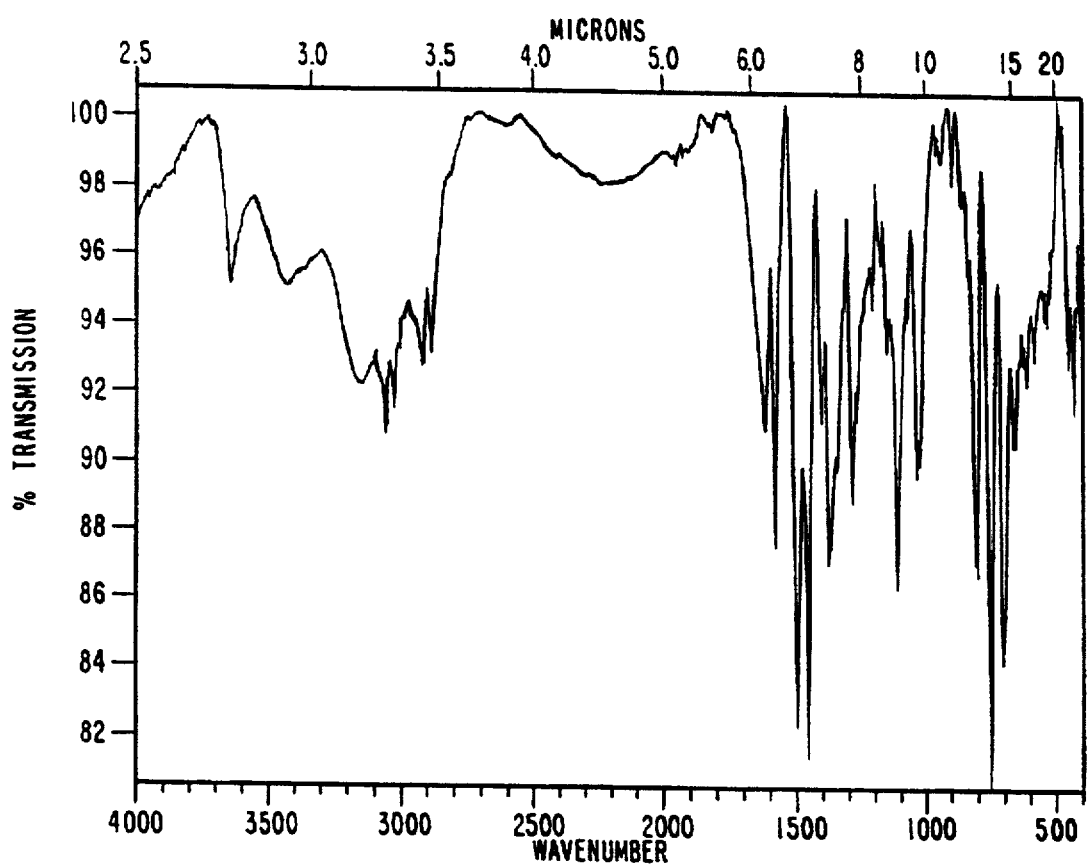
Figure 10A:
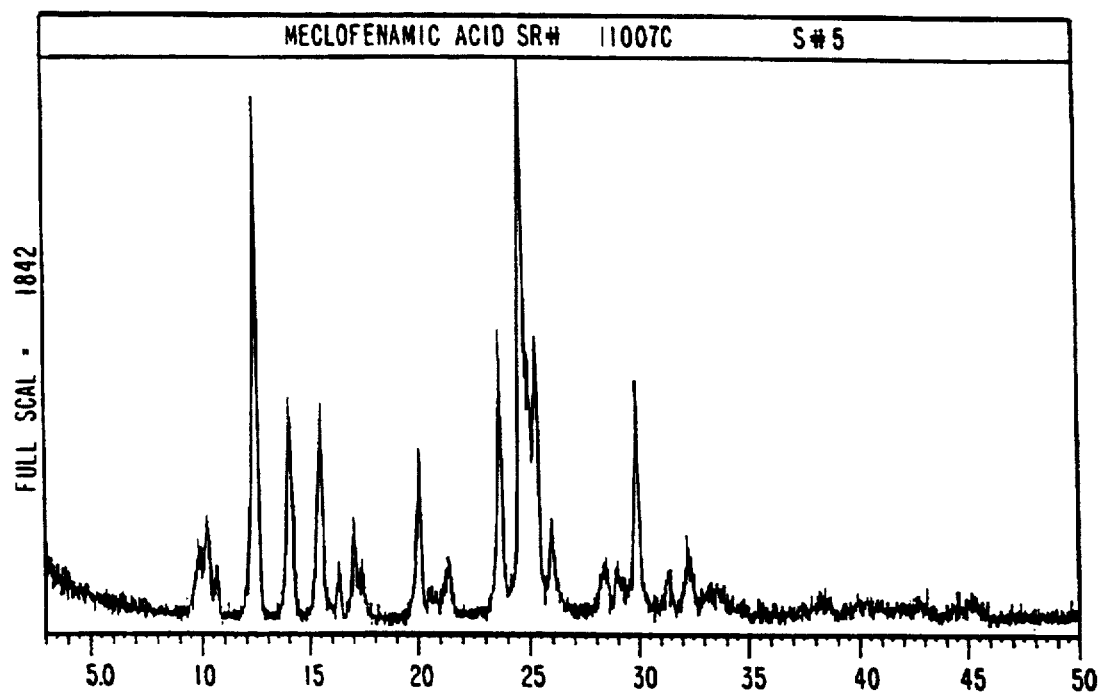
FIGS. 10a and 10b represent comparative X-ray Diffractograms of Meclofenamic Acid/Diphenhydramine salt/ion pair of the present invention, respectively.
Figure 10B:
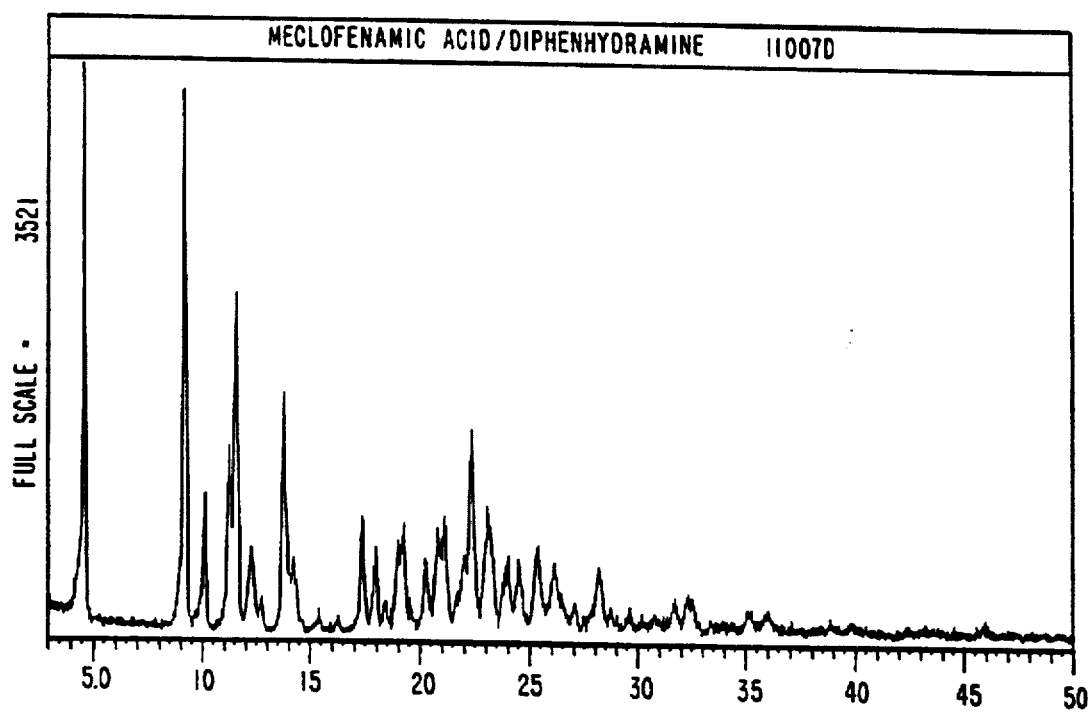

| Elemental Analysis of MA/DPH | | | |
|---|---|---|---|
| | % C | % H | % N |
| Theoretical | 67.45 | 5.98 | 5.08 |
| Experimental | 65.17 | 6.07 | 4.82 |
| Theoretical (with 1 mole of water) | 65.38 | 6.01 | 4.92 | e) Proton Nuclear Magnetic Resonance (NMR) spectra for Meclofenamic acid (MA), Diphenhydramine (DPH), and Meclofenamic acid-Diphenhydramine salts (MA/DPH) are shown in FIG. 9. The presence of water was detected in the MA/DPH and MA samples. An upfield shift for the proton of the carboxylic acid group, a slight downfield shift for the aliphatic protons of DPH, and a slight shift upfield for the aromatic protons of MA peaks was observed for the MA/DPH sample. The shifts in the NMR spectra observed for MA/DPH are indicative that a chemical reaction has occurred, such as a proton transfer.

f) Fourier Transform Infrared Spectroscopy (FTIR) was performed on the compounds using the Cygnus 100 FTIR. Potassium bromide (KBr) pellets were made of both the Meclofenamic acid-Diphenhydramine salt and the individual components as before. The IR spectra for MA and MA/DPH are shown in FIG. 10. The characteristic carbonyl stretching peak of Meclofenamic acid shifted from 1653 nm to 1617 nm in the MA/DPH sample. This shift in the FTIR spectra indicates that a chemical reaction occurred in the formation of the new salt/ion-pair of MA/DPH.

g) The UV absorbance maxima and calculated absorptivities for Meclofenamic acid (MA) and Meclofenamic acid-Diphenhydramine salt (MA/DPH) are shown in Table 5.

TABLE 5

| UV Absorptivity of MA/DPH in Methanol | | |
|---|---|---|
| Compound | Abs. Max.(nm) | Absorptivity (1/g-cm) |
| MA | 280 | 21.21 |
|  | 334 | 22.62 |
| MA/DPH | 286 | 12.01 |
|  | 324 | 10.94 |

Again, the UV spectra clearly shows a shift in both the absorbance maximum ($\lambda$ max) and the absorbtivity between the parent and new compound thereby proving the formation of a new chemical entity.

h) The solubilities of the Meclofenamic acid-Diphenhydramine salt compounds and its individual components were determined at room temperature following the same methodology set forth in Example II. The comparative results are set forth in Table 6.

TABLE 6

| Solubility of MA/DPH in Water | |
|---|---|
| Compound | R.T. Solubility ($\mu$g/ml) |
| DPH | 276 |
| MA/DPH | 97 |
| MA | 30 (4) | i) X-ray Diffraction

Pressed powder samples of the Meclofenamic acid-Diphenhydramine salts and Meclofenamic acid alone were prepared and were scanned at a rate of 5 deg/min from 3 deg to 50 deg (2-theta) with the detector sampling interval set at 0.02 deg. A copper source operating at a 40 kV/40 mA power level was used to generate the x-rays. The x-ray diffractograms obtained for Meclofenamic acid and DPH/Meclofenamic acid are shown in FIG. 11. No major peaks of Meclofenamic acid were found to match those of MA/DPH. Four minor peaks overlapped for MA and MA/DPH indicating that a portion of the original structure of MA remains intact in the MA/DPH. The diffractograms confirm that the crystalline structure of MA/DPH is completely different than that of MA.

It is clear for all of the above physico-chemical data that the novel pharmaceutical compounds of the present invention possess improved characteristics over their individual components alone. The different solubilities, crystalline structures, melting points and other characteristics coupled with the fact that two active ingredients have been combined to allow for a dual action medication enable these compounds to provide symptomatic relief in sustained and enhanced dosage forms.

What we claim is:

1. An improved pharmaceutical composition for multi-symptom relief comprising the salt formed by the acid-base reaction of a non-steroidal anti-inflammatory drug selected from the group consisting of sulindac, ibuprofen, naproxen, dichlofenac and mixtures thereof and an antihistamine selected from the group consisting of diphenhydramine, ranitidine, loratidine, cimetidine, Hismanal, terfenidine and mixtures thereof on a 1:1 molar basis that is administered in a therapeutically effective single dosage form selected from the group consisting of capsules, tablets, elixirs, parenterals, suspensions and sachets.

2. An improved pharmaceutical composition for multi-symptom relief comprising an ion-pair formed by the acid-base reaction of a non-steroidal anti-inflammatory drug selected from the group consisting of sulidac, ibuprofen, naproxen, dichlofenac and mixtures thereof, and an antihistamine selected from the group consisting of diphenhydramine, ranitidine, loratidine, cimetidine, Hismanal, terfenidine and mixtures thereof, on approximately a 1:1 molar basis in a single, therapeutically effective dosage form selected from the group consisting of capsules, tablets, elixirs, parenterals, suspensions and sachets.

3. The pharmaceutical composition of claim 1 or 2 further comprising the addition of pharmaceutically acceptable excipients and non-toxic carrier materials.

* * * * *